United States Patent [19]

Kramann et al.

[11] Patent Number: 4,509,945

[45] Date of Patent: Apr. 9, 1985

[54] CATHETER FOR CATHETERIZING CENTRAL VEINS

[75] Inventors: Bernhard Kramann; Meinhard Rust, both of Munich, Fed. Rep. of Germany

[73] Assignee: Sterimed Gesellschaft für medizinischen Bedarf mbH, Saarbrücken, Fed. Rep. of Germany

[21] Appl. No.: 530,580

[22] PCT Filed: Dec. 17, 1982

[86] PCT No.: PCT/EP82/00270

§ 371 Date: Aug. 16, 1983

§ 102(e) Date: Aug. 16, 1983

[87] PCT Pub. No.: WO83/02064

PCT Pub. Date: Jun. 23, 1983

[30] Foreign Application Priority Data

Dec. 17, 1981 [DE] Fed. Rep. of Germany ....... 3150052

[51] Int. Cl.³ .............................................. A61M 25/00
[52] U.S. Cl. .................................... 604/164; 604/170; 128/657
[58] Field of Search ............................... 604/170–172, 604/95, 164, 165, 269, 267, 280–282; 128/657

[56] References Cited

U.S. PATENT DOCUMENTS

| 2,118,631 | 5/1938 | Wappler . | |
|---|---|---|---|
| 3,539,034 | 11/1970 | Tafeen | 604/164 |
| 3,547,103 | 12/1970 | Cook . | |
| 3,612,038 | 10/1971 | Halligan | 604/281 X |
| 3,757,768 | 9/1973 | Kline . | |
| 4,349,023 | 9/1982 | Gross | 604/164 |
| 4,417,886 | 11/1983 | Frankhouser et al. | 604/164 |

FOREIGN PATENT DOCUMENTS 1208639 10/1970 United Kingdom .

OTHER PUBLICATIONS

Blitt et al., Central Veneous Catheterization via the External Jugular Vein, JAMA, Aug. 12, 1974, vol. 229, No. 7, pp. 817–818.

Primary Examiner—Stephen C. Pellegrino
Attorney, Agent, or Firm—Toren, McGeady and Stanger

[57] ABSTRACT

A novel catheter with a guide wire, the tip of which is bent in the manner of a walking stick, enables central veins to be rapidly and safely catheterized via a peripheral approach.

15 Claims, 5 Drawing Figures

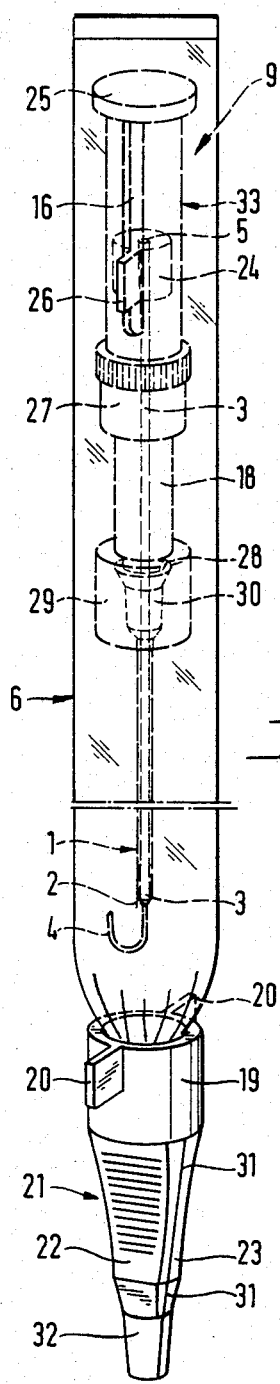

CATHETER FOR CATHETERIZING CENTRAL VEINS

FIELD OF THE INVENTION

The invention relates to a catheter for catheterizing central veins via peripheral vein approaches.

PRIOR ART

Catheterization of central veins (hollow vein, Vena cava) plays an important role in the treatment of shocks, in the determination of the central venous blood pressure or in the monitoring of the latter during surgical interventions, and in parenteral feeding. Depending on the entry point of the catheter into the human body a distinction is made between the central approach routes and the peripheral approach routes. In the first case, approach is via the Vena jugularis, the vena anonyma or the Vena subclavia, whilst in the second case approach is via leg veins or brachial veins. Catheterization via a central approach route has the advantage that the catheter can be laid in a vessel which has a relatively large lumen and no venous valves, and that the distance up to the hollow vein is short. It is a disadvantage of the central approach routes, however, that it is difficult to find the veins which can be used for venipuncture, and that this requires special care because large arteries are located closeby. Thus, the puncture cannula reaches the Vena anonyma only at a depth of about 5 cm. For a puncture of the Vena jugularis, the puncture cannula must be guided through the Musculus sternocleidomastoideus under a certain angle to the skin surface, before it encounters the vein, running directly next to the Arteria carotis, at a depth of 3–4 cm. The catheterization of central veins via a central approach can therefore be carried out, largely without risk, only by particularly experienced and skilled physicians, such as in particular specialist anesthetists. In the case of less experienced practitioners or under unfavorable external circumstances, such as, for example, when treating accident victims at the scene of an accident or in the rescue vehicle or aircraft, approach to the central veins via a peripheral vein, that is to say a leg vein or a brachial vein, is to be preferred, because these veins are in most cases clearly visible through the skin or can be made readily detectable by briefly applying a ligature to the leg or to the upper arm. In the case of approach via a peripheral vein, however, advancing the catheter is more difficult, on the one hand because the distance up to the hollow vein is considerably longer, and on the other hand because the peripheral veins have a smaller internal diameter and, in addition, venous valves must be overcome.

For this reason, difficulties arise in a considerable percentage of catheterizations via a peripheral approach, when advancing the catheter tube: for example, the tip of the tube can take a wrong direction (Via falsa), can catch on venous valves or vessel branches and can cause complications, which are a danger to life, such as embolisms or hemorrhages in the thorax. There is therefore a demand for an improvement in the methods, hitherto practised, of central vein catheterization via peripheral approach, and for an appropriate catheter being made available. It was the object of the invention to provide a new catheter for the catheterization of central veins via peripheral approach, which catheter enables central vein catheterizations to be carried out safely and rapidly, in particular also in emergency situations under the frequently unfavorable environmental conditions of the scene of an accident or in rescue vehicles and aircraft.

DESCRIPTION OF THE INVENTION

It has now been found that the catheterization of the Vena cava superior via peripheral vein approach can be carried out in a substantially better way and without complications, when a catheter is used which is provided with a guide wire, the elastic front end of which is curved in the manner of a walking stick. This result is very surprising since it was assumed hitherto that mandrins curved in this way like a walking stick would be unsuitable for advancing in veins, since they would cause injuries therein, for example to the venous valves.

The subject of the invention is therefore a catheter for catheterizing central veins via peripheral vein approaches, comprising a catheter tube of an internal diameter of 0.5 to 2 mm, an external diameter of 0.7 to 2.4 mm and a length of 400 to 800 mm, with a guide wire which is curved in the manner of a walking stick over a length of 15 to 30 mm at its distal end. Peripheral vein approaches are understood in particular as the approaches via the veins in the region of the angle of the elbow and the back of the hand.

To simplify the introduction of the catheter tube into the vein cannula, a new displacement device is proposed according to the invention, wherein the mutual displaceability of the catheter tube and guide wire is limited by stop arrangements. The mutual displacement length preferably corresponds approximately and at least to the length of the curved distal end of the guide wire. In the front stop position, the curved end of the guide wire protrudes from the distal end of the catheter tube. In the rear stop position, the curved end of the guide wire is in a withdrawn position in the distal end of the catheter tube.

FIGS. 1 and 5 show vein catheters packaged ready for use.

Figure 1:
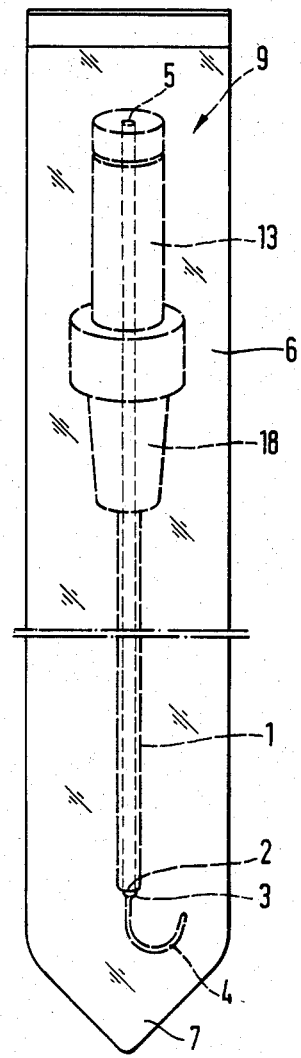

In the text which follows, the invention is explained in more detail by reference to FIGS. 1 to 5:

FIG. 1 shows, in a simplified manner, an embodiment of the catheter according to the invention, packaged in a plastic cover 6, the distal end 7 of which can be formed with a pointed end, if desired, in which case the tip of the distal end 7 can be cut off when the catheter is used or can be designed to be pierceable by the tip 2 of the catheter. The curved end 4 of the guide wire 3 protrudes from the distal end 2 of the catheter tube 1.

Figure 2:
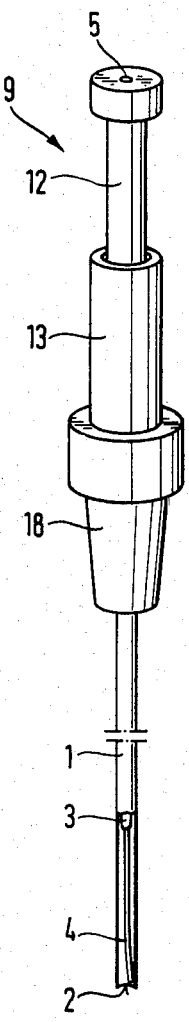
FIG. 2 shows a catheter with the guide wire withdrawn.

FIG. 2 diagrammatically shows the catheter with the curved distal end 4 of the guide wire 3 drawn into the catheter tube 1. The two sleeves 12, 13 of the displacement device 9 are here pulled apart into an end position, namely the rear stop position.

Figure 3:
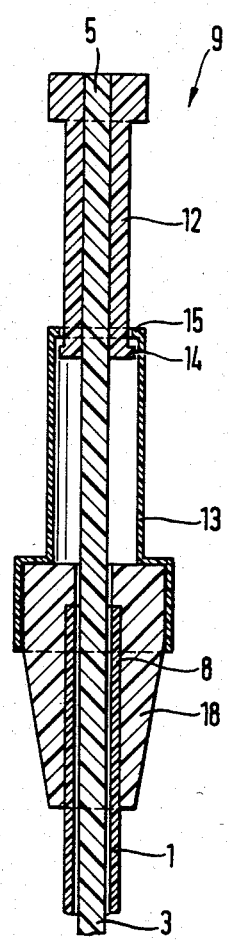
FIGS. 3 and 4 show displacement devices.

FIG. 3 shows a schematized cross-section through an embodiment of the displacement device 9. The inner sleeve 12 with a peripheral edge bead 14 surrounds the proximal end 5 of the guide wire 3. The female sleeve 13 with a corresponding internal edge bead 15 at the proximal end 5 is removably placed onto the catheter junction piece 18 of the catheter tube 1 by its distal end which in this embodiment is widened, even though this does not necessarily have to be the case. The proximal end 8 of the catheter tube 1 is rigidly joined to the catheter junction piece 18, for example it is glued in or molded on the catheter junction piece. After the catheter has been introduced via a peripheral vein approach and the catheter tip 2 has reached its destination in the central venous system, the plastic cover 6, indicated in FIG. 1, is separated together with the displacement device 9 including the guide wire 3 in the proximal direction from the catheter junction piece 18. If desired, a syringe, an infusion bottle or a pressure-measuring instrument, for example, can then be connected to the catheter junction piece 18 via a conventional adaptor with appropriate fittings which are preferably conical.

Figure 4:
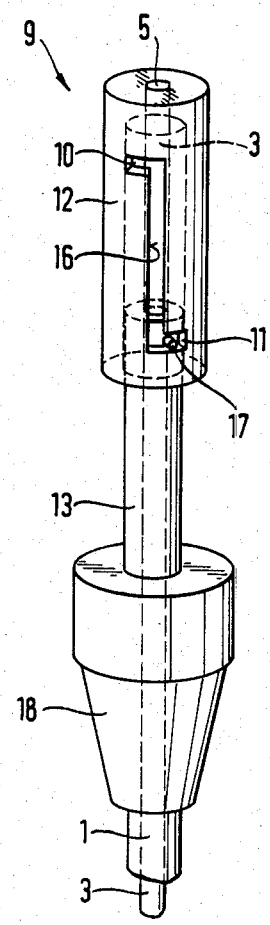

FIG. 4 shows an alternative embodiment of the displacement device 9, the outer sleeve having an axial guide slot 16 with two engagement slots at the end, preferably arranged perpendicular thereto, as stop devices 10, 11 and the inner sleeve 13 having a stop pin 17.

FIG. 5 shows, similarly to FIG. 1, a vein catheter which is packaged ready for use in a plastic cover. In this embodiment, however, the plastic cover 6 ends in a sleeve 19. The sleeve 19 which, if desired, is fitted with holding wings 20, is slipped over a catheter insertion part 21 known per se. The catheter insertion part 21 consists of two portions 22, 23 which can be separated from one another along the parting line 31, as soon as the sleeve 19 has been drawn off. In this case, the displacement device 9 consists of an external sleeve 33 which is closed by a cover 25 at the proximal end and has an axial guide slot 16 and in which a piston 24 is movably mounted. The piston 24 is rigidly joined to the proximal end 5 of the guide wire 3 and carries a displacement knob 26. It is self-evident that the sleeve 33, can have, diametrically opposite the guide slot 16, a second guide slot 16 in which a second displacement knob 26 of the piston 24 is correspondingly guided. The displacement device 9 is releasably screwed to the catheter junction piece 18 by means of a cap nut 27 which is formed as a continuation of the sleeve 33 and has an internal thread. Above the connection cone 30 of the catheter junction piece 18, and held in a peripheral groove 28, there is a freely rotatable cap nut 29, by means of which the connection cone 30 of the catheter junction piece 18 can be secured in the junction part of the vein cannula (not drawn) (for example a Luer lock).

The guide wire 3 fills the lumen of the catheter tube 1 as far as possible, but only so far that mutual displacement with the least possible friction is possible. To reduce the friction forces between the catheter tube 1 and the guide wire 3, small quantities of a medically acceptable lubricant, such as, for example, glycerol or preferably silicone oil, can be used. The length of the end 4, curved in the manner of a walking stick, of the guide wire is about 1.5 to 3 cm, preferably about 2 cm. The material, dimensions and physical properties of the catheter tube 1 correspond to those conventional in catheters for central veins. The internal diameter (lumen) of the catheter tube 1 is between 0.5 and 2.0, preferably 0.8 and 1.6 and particularly preferably 1.1 and 1.2 mm. The external diameter of the catheter tube 1 is between 0.7 and 2.4 mm. Preferred external diameters are 1.4, 1.7 and 2.1 mm. The length of the catheter tube 1 should be about 40 to 80 cm, preferably about 60 cm. In order to enable the introduction and position of the catheter tube 1 in the body to be observed radiologically, it is advantageous to provide at least one X-ray contrast strip, preferably at least two X-ray contrast strips distributed over the periphery, on the catheter tube 1 in the axial direction. In order to enable the examiner also to visualize the position or length of advance of the catheter tube 1 without an X-ray picture, it is expedient to provide markings and/or graduations in anatomically determined distances and/or regular distances. For example, a graduation at distances of 50 mm is advantageous. The material and physical properties of the guide wire 3, including the curved distal end 4, correspond to those in conventional catheters for arterial approaches. For example, the guide wire 3 is a plastic-coated metal wire, the metal wire preferably ending even before the start of the curvature of the distal end 4 curved in the manner of a walking stick, or being made completely as a plastic wire. The curvature of the distal end 4 is produced in a conventional manner, for example by appropriate stretching with heating. In order to increase the flexibility of the distal end 4 curved in the manner of a walking stick, it is expedient to set the diameter thereof to approximately half up to approximately three quarters of the diameter of the uncurved portion of the guide wire 3. This measure is a further subject of the invention. The radius of curvature of the distal end 4 is between about 1 and 10 mm.

The catheter according to the invention is advantageously designed in such a way that, under sterile precautions, it can be used directly without the aid of further means. In a special embodiment, the catheter therefore comprises a puncture kit, which permits the puncture of the vein and introduction of the catheter. In this case a puncture kit is advantageous which allows the use of the procedure known to an expert: a flexible plastic cannula is pushed over a steel cannula, the ground tip of the steel cannula being left free. After the puncture has been made, the steel cannula is drawn out of the plastic cannula, while the plastic cannula remains in the vein. The catheter tube is then pushed through the plastic cannula into the vein. As soon as the distal catheter end has reached the desired target position, the plastic cannula can also be withdrawn from the vein.

The catheter tube 1 with the guide wire 3 located therein, advantageously together with the junction piece 18, fitted to the proximal end 8, for syringes or infusion tubes, is supplied sterile in a transparent protective cover 6 which is sealed at both ends. While the catheter is being stored, the curved distal end 4 of the guide wire 3 protrudes from the distal end 2 of the catheter tube 1. This measure prevents adverse effects on the curvature of the curved end 4 of the guide wire 3 during the storage period.

In order to enable the catheter tube 1 in use to be introduced into the cannula seated in the vein, the distal curved end 4 of the guide wire 3, protruding from the catheter tube 1 while in the plastic protective cover 6, is retracted into the catheter tube 1 by pulling the proximal end 5 of the guide wire 3. In the embodiment according to FIG. 1, the plastic protective cover 6 is then opened at its distal end 7, and the distal end 2 of the catheter tube 1 (catheter tip) is introduced into the cannula seated in the vein. After the catheter tip 2 has been advanced through the plastic cannula into the vein by a few centimeters, the curved end 4 of the guide wire 3 is pushed out of the catheter tip 2 again for a length sufficient for it to reassume its curved form.

In the illustrative embodiment according to FIG. 5, the catheter insertion part 21 is connected via the connection cone 32 to the junction piece of the plastic vein cannula (not drawn) and the curved distal end 4 of the guide wire 3 is retracted into the catheter tip 2 by displacing the displacement knob 26 into the rear stop position. The catheter tip 2 is then pushed through the catheter insertion part 21 into the plastic vein cannula. The bore of the catheter insertion part 21 tapers in the direction of the vein cannula like a funnel to an internal diameter which approximately corresponds to the internal diameter of the vein cannula. This design makes it easier to thread the catheter tip 2 into the vein cannula. After the catheter tip 2 has penetrated out of the distal end of the vein cannula and for a few centimeters into the vein, the curved end 4 of the guide wire 3 is pushed out of the catheter tip 2 by displacing the displacement knob 26 in the distal direction into the front stop position. The catheter tube 1 can then be advanced in the vein until the catheter tip has reached the desired place in the hollow vein. The sleeve 19 of the plastic cover 6 is then drawn off from the catheter insertion part 21. The two portions 22, 23 of the catheter insertion part 21 can then be separated from one another and the catheter insertion part 21 can thus be removed. The displacement device 9 is separated from the catheter junction piece 18. The plastic cover 6 and the displacement device 9 including the guide wire 3 are then drawn off in the proximal direction. The connection cone 30 of the catheter junction piece 18 can then be inserted into the connection fitting of the vein cannula and be secured by means of the cap nut 29. The embodiment according to FIG. 5 enables the catheter according to the invention to be introduced with a particularly low level of contamination.

The limited displaceability, according to the invention, which preferably corresponds approximately to the length of the curved distal end 4 of the guide wire 3, can be achieved by various methods having the same effect. For example, the catheter tube 1 and guide wire 3 are each connected to one of two concentric telescopic sleeves 12, 13, the displacement length of which is fixed by stops. The internal one of the two sleeves 12, 13 has a peripheral edge bead 14, for example on the distal end, and the external one of the two sleeves 12, 13 has an internal edge bead 15 as an abutment on the proximal end. In another embodiment of the invention, the external one of the two sleeves 12, 13 has an axial guide slot 16 with two engagement slots 10, 11, perpendicular thereto, at the end, a stop pin 17 of the internal one of the two sleeves 12, 13 running in the guide slot, whereby a mutual fixing of the two sleeves 12, 13 in the two end positions is obtained in the manner of a bayonet-closure. The provision of the mutual limited displacement of the two sleeves 12, 13 by means of one or more thread turns is also regarded as an equivalent effect.

The catheter according to the invention is supplied sterile, preferably together with a venipuncture cannula, in particular a vein cannula, the steel cannula of which is surrounded by a plastic cannula and the steel cannula of which can be removed after the vein has been punctured. As a common packaging, a so-called peel pack is preferred.

The catheter according to the invention enables central veins to be catheterized rapidly and with few complications via peripheral vein approach. A further advantage is that the catheter can be supplied in a kit or package which allows it to be used without the hands of the examiner coming into direct contact with the catheter.

In connection with the present invention, the expressions "proximal" and "distal" are used from the viewpoint of the examiner, that is to say a proximal part of an embodiment according to the invention is, during catheterization, nearer to the examiner than a distal part.

The subject of the invention are the embodiments described above, their equivalents in patent law, and the subjects of the claims.

We claim:

1. A catheter for catheterizing central veins via peripheral vein approaches, comprising a catheter tube (1) having an internal diameter of 0.5 to 2 mm, an external diameter of 0.7 to 2.4 mm and a length of 400 to 800 mm, a J-shaped guide wire (3) disposed axially displaceably in the catheter tube, the guide wire having a resilient distal end (4), which is curved over a length of 15 to 30 mm, and a means (9) for limiting the mutual displaceability of the catheter tube (1) relative to the guide wire (3) approximately to the length of the curved distal end (4) of the guide wire (3).

2. A catheter as claimed in claim 1, wherein the diameter of the curved distal end (4) of the guide wire (3) is smaller than the diameter of the straight portion of the guide wire (3).

3. A catheter as claimed in claim 2, wherein the diameter of the curved distal end (4) of the guide wire (3) is approximately half up to approximately three quarters of the diameter of the straight portion of the guide wire (3).

4. A catheter as claimed in claim 1, wherein, in one end position of displacement, the curved distal end (4) of the guide wire (3) protrudes from the distal end (2) of the catheter tube (1) and, in the other end position of displacement, the curved distal end (4) of the guide wire (3) is completely drawn into the distal end (2) of the catheter tube (1).

5. A catheter as claimed in claim 1 or 4, wherein the means for limited mutual displaceability of the catheter tube (1) relative to the guide wire (3) is provided by two concentric telescopic sleeves (12, 13), of which one is joined to the catheter tube (1) and the other is joined to the guide wire (3).

6. A catheter as claimed in claim 5, wherein the internal one of the two sleeves (12, 13) has a peripheral edge bead (14) as a stop and the external one of the two sleeves (12, 13) has an internal edge bead (15) as an abutment.

7. A catheter as claimed in claim 5, wherein the external one of the two sleeves (12, 13) has an axial guide slot (16) with two engagement slots (10, 11) perpendicular thereto, at the end, a stop pin (17) of the internal one of the two sleeves (12, 13) running in the guide slot.

8. A catheter as claimed in claim 1 or 4, wherein the means limited mutual displaceability of the catheter tube (1) relative to the guide wire (3) is provided by a sleeve (33) which has one or more axial guide slots (16) and in which a piston (24) runs which is joined to the guide wire (3) and has one or more displacement knobs (26) running in the guide slots (16).

9. A catheter as claimed in claim 5, wherein the limited mutual displaceability of the two sleeves (12, 13) is accomplished by one or more thread turns.

10. A catheter as claimed in claim 1, which is surrounded by a plastic cover (6).

11. A catheter as claimed in claim 10, wherein the distal end (7) of the plastic cover (6) is pointed.

12. A catheter as claimed in claim 11, wherein the distal end (7) of the plastic cover (6) is designed to be pierceable by the catheter tip (2).

13. A catheter as claimed in claim 10, wherein the distal end of the plastic cover (6) is joined to a sleeve

(19) which can be slipped over a catheter insertion part (21).

14. A catheter as claimed in claim 1, which is supplied in one package together with a matching venipuncture cannula.

15. A catheter as claimed in claim 14, which is packaged in a peel pack.

* * * * *